(12) United States Patent
Minagawa et al.

(10) Patent No.: US 10,941,374 B2
(45) Date of Patent: Mar. 9, 2021

(54) MEDICAL ANALYSIS DEVICE AND CELL ANALYSIS METHOD

(71) Applicants: SUMITOMO RUBBER INDUSTRIES, LTD., Kobe (JP); YAMAGATA UNIVERSITY, Yamagata (JP)

(72) Inventors: Yasuhisa Minagawa, Kobe (JP); Masaru Tanaka, Yonezawa (JP); Takashi Hoshiba, Yonezawa (JP); Tomokazu Shibuya, Yonezawa (JP)

(73) Assignees: SUMITOMO RUBBER INDUSTRIES, LTD., Kobe (JP); YAMAGATA UNIVERSITY, Yamagata (JP)

( * ) Notice: Subject to any disclaimer, the term of this patent is extended or adjusted under 35 U.S.C. 154(b) by 147 days.

(21) Appl. No.: 15/693,919

(22) Filed: Sep. 1, 2017

(65) Prior Publication Data
US 2018/0087017 A1 Mar. 29, 2018

(30) Foreign Application Priority Data

Sep. 29, 2016 (JP) ................. 2016-191617
Jul. 26, 2017 (JP) ................. 2017-144556

(51) Int. Cl.
*C12M 1/32* (2006.01)
*C12M 1/00* (2006.01)
(Continued)

(52) U.S. Cl.
CPC ........... *C12M 23/12* (2013.01); *B01L 3/5085* (2013.01); *C12M 3/04* (2013.01); *C12M 23/20* (2013.01);
(Continued)

(58) Field of Classification Search
CPC ........ C12M 23/12; C12M 3/04; C12M 23/20; C12M 25/04; B01L 3/5085; G01N 33/5005
(Continued)

(56) References Cited

U.S. PATENT DOCUMENTS 5,202,025 A * 4/1993 Onishi ............... B01D 67/0093
                                                           210/500.35
2002/0155617 A1    10/2002 Pham et al.
(Continued)

FOREIGN PATENT DOCUMENTS

CN      105263995 A      1/2016
CN      105636615 A      6/2016
(Continued)

OTHER PUBLICATIONS

Gach et al., "Micropallet Arrays for the Capture, Isolation and Culture of Circulating Tumor Cells From Whole Blood of Mice Engrafted With Primary Human Pancreatic Adenocarcinoma", Biosensors and Bioelectronics, vol. 54, 2014, (Available online Nov. 18, 2013, pp. 476-483.

*Primary Examiner* — Matthew D Krcha
*Assistant Examiner* — Jacqueline Brazin
(74) *Attorney, Agent, or Firm* — Birch, Stewart, Kolasch & Birch, LLP

(57) ABSTRACT

The present invention provides a medical analysis device and a cell analysis method, which can capture many types of cancer cells, including cancer cells not expressing EpCAM. The present invention relates to a medical analysis device having a well portion, the well portion having a hydrophilic polymer layer formed at least partly on the inner surface thereof, the hydrophilic polymer layer having fibronectin adsorbed thereto.

5 Claims, 1 Drawing Sheet

(51) Int. Cl.
*C12M 3/04* (2006.01)
*C12M 1/12* (2006.01)
*B01L 3/00* (2006.01)
*G01N 33/50* (2006.01)

(52) U.S. Cl.
CPC ......... *C12M 25/04* (2013.01); *G01N 33/5005* (2013.01); *B01L 3/5021* (2013.01); *B01L 2300/0829* (2013.01); *B01L 2300/16* (2013.01); *B01L 2300/161* (2013.01); *C12N 2533/56* (2013.01)

(58) Field of Classification Search
USPC ........................................................ 422/407
See application file for complete search history.

(56) References Cited

U.S. PATENT DOCUMENTS

| | | | | |
|---|---|---|---|---|
| 2003/0190405 | A1* | 10/2003 | Bowers | C08F 246/00 427/2.1 |
| 2006/0160066 | A1 | 7/2006 | Bhatia et al. | |
| 2008/0008736 | A1 | 1/2008 | Glauser | |
| 2010/0261159 | A1 | 10/2010 | Hess et al. | |
| 2011/0123414 | A1* | 5/2011 | Ahern | B01L 3/5082 422/550 |
| 2012/0108468 | A1* | 5/2012 | Keselowsky | G01N 33/54366 506/18 |
| 2013/0210140 | A1* | 8/2013 | Burns | C12N 5/0068 435/366 |
| 2014/0335610 | A1* | 11/2014 | Fukumori | C12M 25/06 435/347 |
| 2016/0011192 | A1* | 1/2016 | Wagner | G01N 33/564 435/7.92 |
| 2018/0201892 | A1* | 7/2018 | Gomi | C12Q 1/045 |
| 2020/0056137 | A1* | 2/2020 | Anzai | C12N 5/0068 |
| 2020/0056138 | A1* | 2/2020 | Anzai | C12M 23/20 |
| 2020/0056154 | A1* | 2/2020 | Anzai | C12M 23/20 |
| 2020/0056155 | A1* | 2/2020 | Anzai | C12N 5/0667 |

FOREIGN PATENT DOCUMENTS

| | | |
|---|---|---|
| JP | 2004-522937 A | 7/2004 |
| JP | 2005-523981 A | 8/2005 |
| JP | 2015-514396 A | 5/2015 |
| JP | 2016-514950 A | 5/2016 |
| JP | 2016-131561 A | 7/2016 |
| WO | WO 02/20825 A1 | 3/2002 |
| WO | WO 03/093357 A1 | 11/2003 |
| WO | WO 2011/157805 A1 | 12/2011 |
| WO | WO 2011/161480 A1 | 12/2011 |
| WO | WO 2013/134788 A1 | 9/2013 |
| WO | WO 2014/117021 A2 | 7/2014 |
| WO | WO 2015/137259 A1 | 9/2015 |
| WO | WO 2016/103002 A1 | 6/2016 |

\* cited by examiner

A-A cross-sectional view

MEDICAL ANALYSIS DEVICE AND CELL ANALYSIS METHOD

TECHNICAL FIELD

The present invention relates to a medical analysis device and a cell analysis method, which can capture specific cells present in blood or biological fluid (e.g., cancer cells present in blood or biological fluid).

BACKGROUND ART

When cancer cells are formed, they are known to appear in due course in blood or biological fluid. Such cancer cells in blood are called "circulating tumor cells (CTCs)". Thus, it can be expected that the circulating tumor cells are examined, e.g., to confirm the cancer-treating effect, predict prognosis life expectancy, predict the effect of anticancer drugs before administration, or examine treatment methods through genetic analysis of cancer cells.

However, a problem exists in that since the number of circulating tumor cells is very small (several to hundreds of cells/1 mL of blood), such cancer cells are difficult to capture.

For example, the CellSearch System is known as a technique for capturing circulating tumor cells. This technique, which utilizes an antigen-antibody reaction (capture by EpCAM antibody), can only capture cancer cells expressing EpCAM, and the types of capturable cancer cells are limited.

CITATION LIST

Patent Literature

Patent Literature 1: JP 2005-523981 T

SUMMARY OF INVENTION

Technical Problem

The present invention aims to solve the above problem and provide a medical analysis device and a cell analysis method, which capture many types of cancer cells, including cancer cells not expressing EpCAM.

Solution to Problem

The present invention relates to a medical analysis device having a well portion, the well portion having a hydrophilic polymer layer formed at least partly on an inner surface thereof, the hydrophilic polymer layer having fibronectin adsorbed thereto.

The hydrophilic polymer layer is preferably formed of at least one hydrophilic polymer selected from the group consisting of poly(meth)acryloylmorpholine and a polymer represented by the formula (I):

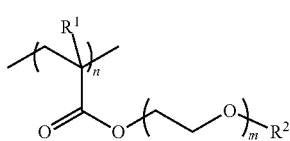

wherein $R^1$ represents a hydrogen atom or a methyl group, $R^2$ represents an alkyl group, m represents 1 to 5, and n represents the number of repetitions.

The hydrophilic polymer layer is preferably formed of a copolymer of at least one hydrophilic monomer selected from the group consisting of (meth)acryloylmorpholine and a compound represented by the formula (I-1):

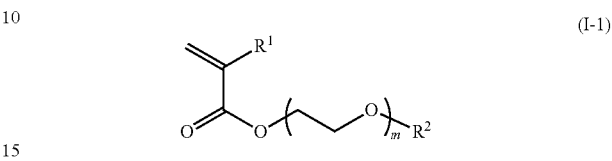

wherein $R^1$, $R^2$, and m are as defined above, with a second monomer.

The medical analysis device preferably further includes a component having fibrinogen adsorbed thereto.

The present invention also relates to a cell analysis method for examining cells present in blood or biological fluid using the medical analysis device described above.

In the cell analysis method, the blood or biological fluid is preferably brought into contact with a component having fibrinogen adsorbed thereto before being introduced into the medical analysis device.

The component having fibrinogen adsorbed thereto is preferably a blood collection syringe, a blood collection tube, or a centrifuge tube.

In the cell analysis method, the blood or biological fluid is preferably centrifuged to remove at least one of a supernatant or a sediment before being introduced into the medical analysis device.

Advantageous Effects of Invention

The medical analysis device according to the present invention has a well portion. The well portion has a hydrophilic polymer layer formed at least partly on the inner surface thereof, and the hydrophilic polymer layer has fibronectin adsorbed thereto. Such a medical analysis device can capture many types of cancer cells, including cancer cells not expressing EpCAM. Thus, for example, it is possible to sufficiently capture specific cells such as cancer cells from blood or biological fluid while reducing the adhesion or attachment of other proteins and cells, thereby selectively capturing the cells such as cancer cells.

DESCRIPTION OF EMBODIMENTS

The present invention relates to a medical analysis device having a well portion. The well portion has a hydrophilic polymer layer formed at least partly on the inner surface thereof, and the hydrophilic polymer layer has fibronectin adsorbed thereto.

Since a hydrophilic polymer layer is not simply formed at least partly on the inner surface of the well portion but fibronectin is further adsorbed to the hydrophilic polymer layer, the hydrophilic polymer displays a significantly improved ability to adhere (adsorb) to specific cells such as cancer cells. Accordingly, the ability to capture specific cells such as cancer cells is greatly improved while reducing the ability to capture other cells such as platelets. As a result, an effect which could never be produced when proteins are present at high levels is achieved in selectively capturing specific cells.

Specifically, since the number of tumor cells (e.g. cancer cells) appearing in biological fluid, such as circulating tumor cells (several to hundreds of cells/1 mL of blood), is very small, it is important to capture as many tumor cells present in the sampled biological fluid as possible to analyze them. In the present invention, since a hydrophilic polymer layer is not simply formed but fibronectin that promotes adhesion (adsorption) of tumor cells is further adsorbed to the surface of the hydrophilic polymer layer, more tumor cells or other specific cells in biological fluid such as blood can be adsorbed or adhered to the hydrophilic polymer layer by bringing the biological fluid into contact with the hydrophilic polymer layer. Then, it can be expected that the number of adsorbed specific cells such as tumor cells is counted to determine the number of specific cells in the blood or biological fluid, e.g., in order to confirm the cancer-treating effect. Moreover, the captured specific cells may be cultured and then used to determine the effect of drugs such as anticancer drugs. This allows us to determine the effect of drugs such as anticancer drugs ex vivo before administration, and also helps to screen drugs such as anticancer drugs.

Examples of preferred embodiments of the present invention are described below with reference to drawings.

Figure 1A:
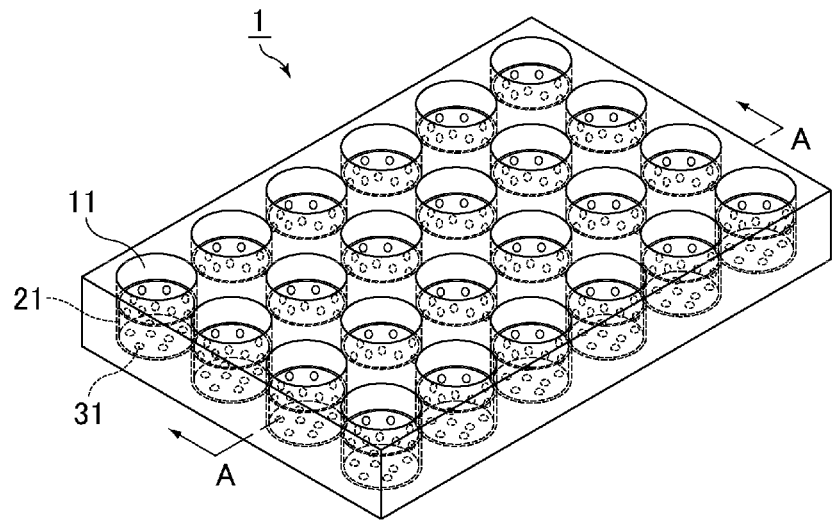
FIGS. 1A, 1B and 1C are exemplary schematic views of a multi-well plate or a single well (medical analysis device) having a well portion having a fibronectin-adsorbed hydrophilic polymer layer formed on the inner surface thereof.
Figure 1B:
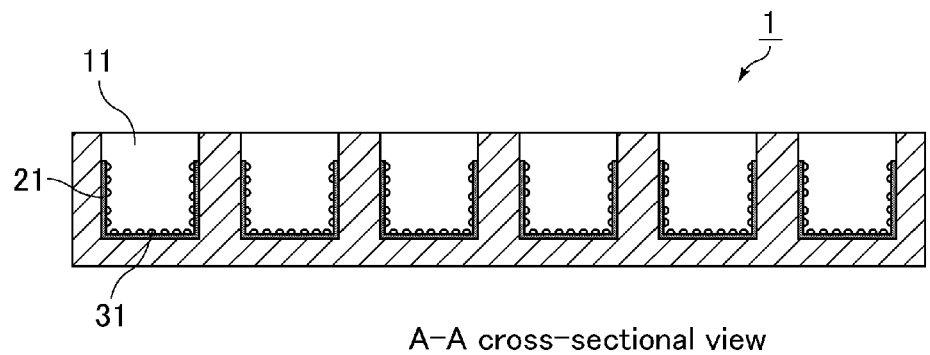

A medical analysis device 1 (multi-well plate 1) illustrated in FIGS. 1A and 1B is a device intended to capture specific cells such as cancer cells in which wells 11 are arranged in so-called matrix form. The multi-well plate 1 has multiple wells 11 having a circular opening. The wells 11, which are recesses into which blood, biological fluid, or others are injected, can be used to confirm the presence or absence of specific cells in the injected blood or biological fluid, count the number of specific cells, culture the specific cells, determine the effect of drugs, and screen the drugs.

Although FIGS. 1A and 1B show a 24-well plate having 24 wells 11 arranged in 4 rows by 6 columns as an example, it is sufficient for the multi-well plate 1 to have at least two wells 11, and any number of wells 11 may be provided. Examples other than the 24-well plate include general multi-well plates in which the number of wells 11 is 6, 96, 384, etc.

Figure 1C:
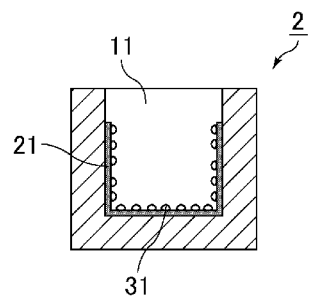

As to the number of wells 11, there may be a single well 2 (medical analysis device 2) (FIG. 1C).

The material of the multi-well plate 1 or single well 2 should be highly transparent for observation during the cell analysis, and examples include acrylic resins (polyacrylic resins) such as polymethyl acrylate, polymethyl methacrylate, polyacrylic acid, and polymethacrylic acid, cycloolefin resins (polycycloolefins), carbonate resins (polycarbonates), styrene resins (polystyrenes), polyester resins such as polyethylene terephthalate (PET), polydimethylsiloxanes, and glass (e.g. borosilicate glass, soda-lime glass). The material should be highly hydrophilic for coating with a hydrophilic polymer, and preferred are polyacrylic resins and soda-lime glass.

Each well 11 is a non-through hole which is opened at the surface of the multi-well plate 1 or single well 2. Blood or biological fluid is injected into the wells 11 through the respective openings. If the presence of specific cells such as cancer cells is confirmed, a culture fluid for culturing the specific cells may also be injected.

The diameter R and depth D of the opening of each well 11 are not particularly limited, and may be those of a conventional multi-well plate 1. Although in FIG. 1, the inner side surface of each well 11 is substantially vertical to the opposite sides of the multi-well plate 1 or single well 2, the inner side surface of each well 11 may be inclined to taper from the opening to the bottom. Alternatively, the inner side surface may be inclined to flare out from the opening to the bottom.

Though the wells 11 in FIG. 1 are circularly opened, the opening of the wells 11 may be of any shape such as a quadrangle.

The multi-well plate 1 may suitably be one in which the multiple wells 11 are separable. Since multiple wells are provided, they can be separated into wells for counting the number of specific cells and for culturing specific cells. For example, the presence or absence of cancer cells is first confirmed in the wells for counting, and if the presence is confirmed, the cancer cells are cultured in the wells for culturing and then used to determine the effect of drugs.

In the multi-well plate 1 (medical analysis device 1) or single well 2 (medical analysis device 2), each well 11 has a hydrophilic polymer layer formed at least partly on the inner surface thereof, and the hydrophilic polymer layer has fibronectin adsorbed thereto. FIG. 1 illustrate a case where a hydrophilic polymer layer 21 is formed on the bottom surface and a part of the side surface of the wells, and fibronectin 31 is adsorbed to the hydrophilic polymer layer 21.

Once blood or biological fluid is introduced into the wells 11, specific cells such as cancer cells present in the blood or biological fluid are adsorbed onto the hydrophilic polymer layer 21 with adsorbed fibronectin 31, while the adsorption of other cells such as platelets and erythrocytes is reduced. Thus, specific cells can be adsorbed onto the hydrophilic polymer layer 21 by introducing and retaining blood or biological fluid in the wells for a predetermined time, followed by washing. Then, it can be expected that the number of adsorbed specific cells is counted to determine the number of specific cells such as cancer cells in the blood or biological fluid, e.g., in order to confirm the cancer-treating effect.

The thickness (film thickness) of the hydrophilic polymer layer 21 (layer formed of a hydrophilic polymer) is preferably 2 to 200 nm, more preferably 20 to 180 nm. When the thickness is adjusted within the range indicated above, selective adsorption or adhesion of cancer cells and low adsorption of other proteins and cells can be well achieved.

The hydrophilic polymer may be appropriately selected from polymers having hydrophilicity. For example, it may be a homopolymer or copolymer of one or two or more hydrophilic monomers, or a copolymer of one or two or more hydrophilic monomers with a second monomer. Examples of the homopolymer and copolymers include polyacrylic acid, polyacrylic acid esters, polymethacrylic acid, polymethacrylic acid esters, polyacryloylmorpholine, polymethacryloylmorpholine, polyacrylamide, and polymethacrylamide.

The hydrophilic monomer may be any monomer containing a hydrophilic group. Examples of the hydrophilic group include known hydrophilic groups such as an amide group, a sulfuric acid group, a sulfonic acid group, a carboxylic acid group, a hydroxy group, an amino group, and an oxyethylene group.

Specific examples of the hydrophilic monomer include (meth)acrylic acid, (meth)acrylic acid esters (e.g. alkoxyalkyl (meth)acrylates such as methoxyethyl (meth)acrylate, and hydroxyalkyl (meth)acrylates such as hydroxyethyl (meth)acrylate), (meth)acrylamide, and (meth)acrylamide derivatives containing cyclic groups (e.g. (meth)acryloylmorpholine).

The second monomer may be appropriately selected as long as it does not inhibit the effect of the hydrophilic polymer. Examples include aromatic monomers such as styrene, vinyl acetate, and N-isopropylacrylamide which can impart temperature responsiveness.

In particular, the hydrophilic polymer is preferably at least one selected from the group consisting of poly(meth)acryloylmorpholine and a polymer represented by the following formula (I):

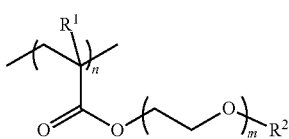

(I)

wherein $R^1$ represents a hydrogen atom or a methyl group, $R^2$ represents an alkyl group, m represents 1 to 5, and n represents the number of repetitions.

The alkyl group represented by $R^2$ preferably has a carbon number of 1 to 10, more preferably 1 to 5. In particular, $R^2$ is particularly preferably a methyl group or an ethyl group. The symbol m is preferably 1 to 3, while n (number of repeating units) is preferably 15 to 1,000, more preferably 30 to 500.

Alternatively, the hydrophilic polymer may also suitably be a copolymer of at least one hydrophilic monomer selected from the group consisting of (meth)acryloylmorpholine and a compound represented by the following formula (I-1):

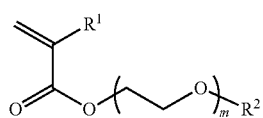

(I-1)

wherein $R^1$, $R^2$, and m are as defined above, with a second monomer.

From the standpoint of selective adsorption or adhesion to cancer cells, the hydrophilic polymer preferably has a weight average molecular weight (Mw) of 4,000 to 150,000, more preferably 5,000 to 100,000, still more preferably 8,000 to 50,000. The Mw as used herein can be determined by gel permeation chromatography (GPC) (GPC-8000 series produced by TOSOH Corporation, detector: differential refractometer, column: TSKGEL SUPERMULTIPORE HZ-M produced by TOSOH Corporation) calibrated with polystyrene standards.

In order to adsorb fibronectin 31 onto the hydrophilic polymer layer 21, a liquid such as a solution or dispersion may suitably be used which preferably has a fibronectin concentration adjusted to 0.5 to 500 µg/ml, more preferably 1 to 250 µg/ml. When the concentration is adjusted within the range indicated above, selective adsorption or adhesion of cancer cells, and low adsorption of other proteins and cells can be well achieved.

The medical analysis device of the present invention can be produced, for example, by preparing a multi-well plate 1 or single well 2 including a well(s) 11 in which a hydrophilic polymer layer 21 with fibronectin 31 adsorbed thereto is formed on the inner surface as illustrated in FIG. 1, optionally followed by addition of other components (parts).

Specifically, when it is desired to produce a multi-well plate 1 or single well 2 with a hydrophilic polymer layer 21 formed thereon, the multi-well plate or single well provided with a polymer layer formed of a hydrophilic polymer can be produced by dissolving or dispersing a hydrophilic polymer in any solvent to prepare a hydrophilic polymer solution or dispersion, and entirely or partially coating the inner surface of each well 11 with the hydrophilic polymer solution or dispersion by a known method, such as (1) by injecting the hydrophilic polymer solution or dispersion into the well(s) 11 and retaining it for a predetermined time, or (2) by applying (spraying) the hydrophilic polymer solution or dispersion to the inner surface of the well(s) 11.

The solvent, injection method, application (spraying) method, and other conditions may be conventionally known materials or methods.

The retention time in the method (1) or (2) may be selected appropriately according to the size of the wells 11, the type of liquid introduced, and other factors, and is preferably five minutes to ten hours, more preferably ten minutes to five hours, still more preferably 15 minutes to two hours. After the retention, the excess hydrophilic polymer solution or dispersion may be discharged followed by drying, as required.

Next, fibronectin 31 may be adsorbed to the formed hydrophilic polymer layer 21 by any known method, such as for example by bringing the hydrophilic polymer layer 21 into contact with a buffer solution (e.g. phosphate buffered saline (PBS)) containing fibronectin 31 by a known method, and leaving them at a predetermined temperature for a predetermined time, optionally followed by washing. The temperature and time may be selected as appropriate, and may be, for example, about 10 to 60° C. and about 0.1 to 10 hours, respectively.

Then, other components, if necessary, are added to the prepared multi-well plate 1 or single well 2 in which a hydrophilic polymer layer 21 with fibronectin 31 adsorbed thereto is formed partly on the inner surface of the well(s) 11, to produce a medical analysis device.

In the present invention, a component having fibrinogen adsorbed thereto is preferably used as another component. When the blood or biological fluid to be analyzed is brought into contact with the component with adsorbed fibrinogen which plays a role in adhesion of blood cells, the number of blood cells is reduced prior to the analysis, thereby resulting in improved adhesion or adsorption of specific cells such as cancer cells.

The cell analysis method of the present invention is for examining cells present in blood or biological fluid using the medical analysis device described above. As mentioned above, the medical analysis device of the present invention has an improved ability to capture specific cells such as cancer cells while reducing the ability to capture other cells such as platelets, and thus has the effect of selectively capturing specific cells such as cancer cells. It can therefore be expected that such a device is used to examine cells present in blood or biological fluid, e.g. in order to confirm the cancer-treating effect, determine the effect of drugs such as anticancer drugs ex vivo, and/or screen drugs such as anticancer drugs, as described above.

In the cell analysis method, in order to reduce the number of blood cells in advance to improve adhesion or adsorption of specific cells such as cancer cells, the blood or biological fluid is preferably brought into contact with the component having fibrinogen adsorbed thereto before being introduced (e.g. injected or added dropwise) into the medical analysis device. For example, when the component having fibrinogen adsorbed thereto is a blood collection syringe, a blood collection tube, or a centrifuge tube, the above-mentioned effects can be significantly achieved.

In the cell analysis method, in order to reduce the number of blood cells in advance to improve adhesion or adsorption of specific cells such as cancer cells, the blood or biological fluid is preferably centrifuged to remove the supernatant and/or the sediment before being introduced (e.g. injected or added dropwise) into the medical analysis device.

EXAMPLES

The present invention is specifically described with reference to examples below, but is not limited thereto.

Example 1

2-methoxyethyl acrylate was thermally polymerized at 80° C. for six hours using azobisisobutyronitrile (AIBN) to produce poly(2-methoxyethyl acrylate) (molecular weight Mn=about 15,000, Mw=about 50,000). Then, a 2.5 w/v % solution of the poly(2-methoxyethyl acrylate) in methanol was prepared.

The poly(2-methoxyethyl acrylate) solution (2.5 w/v %) was injected into a commercially available PMMA plate, and left for 30 minutes at room temperature. Thereafter, the solution was drawn using a pipette, followed by drying to form a hydrophilic polymer layer.

Further, fibronectin was adsorbed to the part coated with poly(2-methoxyethyl acrylate) (hydrophilic polymer layer). Specifically, a 1 μl/ml solution of fibronectin in a PBS solution (phosphate buffered saline) was prepared, brought into contact with the hydrophilic polymer layer, and left at 40° C. for one hour, followed by washing with a PBS solution to prepare an analysis device including a multi-well plate with a fibronectin-adsorbed hydrophilic polymer layer formed thereon as illustrated in FIG. 1.

Example 2

An analysis device was prepared in the same manner as in Example 1, except that the concentration in the PBS solution was changed to 10 μl/ml.

Example 3

An analysis device was prepared in the same manner as in Example 1, except that the concentration in the PBS solution was changed to 100 μl/ml.

Example 4

An analysis device was prepared in the same manner as in Example 2, except that a pipette (fibrinogen-adsorbed blood collection tube) was separately prepared by coating the inner surface of a pipette with a 10 μl/ml fibrinogen solution, followed by washing with a PBS solution and then sufficient dehydration.

Example 5

An analysis device was prepared in the same manner as in Example 1, except that the concentration in the PBS solution was changed to 200 μl/ml.

Comparative Example 1

An analysis device was prepared in the same manner as in Example 1, except that a poly(2-methoxyethyl acrylate) layer was simply formed.

The medical analysis devices prepared in the examples and comparative example were evaluated as follows. The medical analysis device of Example 4 was evaluated in the same manner, except that blood was previously sucked up with the prepared pipette, kept in the pipette for 10 minutes, and then injected into the wells.

(Thickness of Hydrophilic Polymer Layer (Coating Layer))

The thickness of the hydrophilic polymer layer on the inner surface of the wells was measured (photographed) using a TEM at an accelerating voltage of 15 kV and a magnification of 1,000 times.

(Amount of Adsorbed Platelets)

A liquid prepared by mixing plasma with platelets to adjust the platelet concentration (plating density) to $4\times10^7$ cells/cm$^2$ was injected into the wells and left at 37° C. for one hour. The inside of the wells was washed with phosphate buffered saline, followed by fixation using 1% glutaraldehyde (being left at 37° C. for two hours). Then, the inside of the wells was washed again with phosphate buffered saline and distilled water.

The prepared sample was observed by SEM, and the number of adsorbed platelets was counted. The numbers are compared relative to Comparative Example 1 set equal to 1.0.

(Counting of Number of Cancer Cells)

Fibrosarcoma (HT-1080) was suspended in a dissociation solution and a portion of the suspension was resuspended in a PBS solution to count the number of cells using a blood cell counter. Using the obtained number, the dissociation solution containing fibrosarcoma (HT-1080) was resuspended in blood so that the calculated plating density (concentration) was 2,850 cells/cm$^2$.

A 1 ml portion of this blood was injected into each well and left at 37° C. for one hour to cause adhesion. Then, non-adhering cells were washed away with a PBS solution. Subsequently, immunostaining was performed, and the number of adhering cancer cells was counted using a fluorescence microscope. The numbers of adhering cells are compared relative to Comparative Example 1 set equal to 1.0.

(Analysis of Whole Blood Spiked with Cancer Cells)

Stained human colon adenocarcinoma (HT-29) cells were suspended in whole blood at a concentration of 100 cells per ml of blood to prepare a spiked blood sample. The sample was diluted with an equal volume of a liquid medium to prepare a spiked blood dilution. Next, to a 15 ml centrifuge tube was added Lymphoprep (a solution for the isolation of mononuclear cells, density=1.077±0.001 g/mL) and then the spiked blood dilution, followed by centrifugation at 800 g for 20 minutes. Then, the mononuclear cell layer was separated. To the separated mononuclear cell layer was added a phosphate buffer (PBS) solution, followed by centrifugation again to concentrate the mononuclear cell layer. After the centrifugation, the aggregates at the lowermost layer were suspended in a liquid medium containing 10% fetal bovine serum (FBS) in a volume equal to the initial whole blood volume. A 1 ml portion of the suspension was injected into each well and left at 37° C. for one hour to cause adhesion. Then, non-adherent cells were washed away with a PBS solution. Thereafter, the number of adhering cancer cells was counted using a fluorescence microscope. The numbers of adhering cells are compared relative to Comparative Example 1 set equal to 1.00.

TABLE 1

| | Example | | | | Comparative Example |
| --- | --- | --- | --- | --- | --- |
| | 1 | 2 | 3 | 4 | 1 |
| Thickness of hydrophilic polymer layer (nm) | 88 | 88 | 88 | 88 | 88 |
| Fibronectin concentration (µg/ml) | 1 | 10 | 100 | 10 | — |
| Amount of adsorbed plateletes | 0.8 | 0.4 | 0.3 | 0.1 | 1.0 |
| Amount of adhering cancer cells | 3.3 | 4.5 | 4.0 | 5.6 | 1.0 |
| Selectivity | 4.1 | 11.3 | 13.3 | 56 | 1.0 |

Selectivity = (amount of adhering cancer cells)/(amount of adsorbed platelets)

TABLE 2

| | Example | | Comparative Example |
| --- | --- | --- | --- |
| | 4 | 5 | 1 |
| Thickness of hydrophilic polymer layer (nm) | 88 | 88 | 88 |
| Fibronectin concentration (µg/ml) | 10 | 200 | — |
| Number of adhering cancer cells in analysis of spiked blood | 1.55 | 1.53 | 1.00 |

In Examples 1 to 3 in which a hydrophilic polymer layer with fibronectin adsorbed thereto was formed, the amount of adhering cancer cells was greatly improved as compared to Comparative Example 1 in which a hydrophilic polymer layer was simply formed. This is presumably because preferential adhesion of cancer cells was caused due to the fibronectin, a protein playing a role in adhesion of cancer cells, adsorbed onto the poly(2-methoxyethyl acrylate) layer.

In Example 4 in which further blood was previously brought into contact with a container having fibrinogen adsorbed to its surface (the inner surface of a pipette), the amount of adhering cancer cells was further improved. This is presumably because since blood was injected into the pipette having fibrinogen, which plays a role in adhesion of blood cells, adsorbed to the inner surface of the container before being added dropwise to the wells, the number of blood cells was reduced, thereby further improving adhesion of cancer cells.

Moreover, in the examples, since the amount of adsorbed platelets was small while the amount of adhering cancer cells was large, good selectivity [(amount of adhering cancer cells)/(amount of adsorbed platelets)] was also exhibited.

As shown in Table 2, Example 4, which exhibited good adhesion of cancer cells in Table 1, and Example 5, in which an increased amount of fibronectin was adsorbed, were also excellent in adhesion of cancer cells in the analysis of whole blood spiked with cancer cells.

REFERENCE SIGNS LIST

1: Medical analysis device (multi-well plate)
11: Well
21: Hydrophilic polymer layer
31: Fibronectin

The invention claimed is:

1. A medical analysis device, comprising a well portion, the well portion having a hydrophilic polymer layer formed at least partly on an inner surface of the well portion, the hydrophilic polymer layer having fibronectin adsorbed on the hydrophilic polymer layer,
wherein the hydrophilic polymer layer is at least one hydrophilic polymer selected from the group consisting of a homopolymer of 2-methoxyethyl acrylate, and a copolymer of 2-methoxyethyl acrylate with at least one monomer selected from the group consisting of styrene, vinyl acetate, and N-isopropylacrylamide.

2. A cell analysis method for examining cells present in blood or biological fluid, comprising the steps of: obtaining blood or biological fluid, injecting the blood or biological fluid into the well portion of the medical analysis device according to claim 1, and confirming the presence or absence of cells in the injected blood or biological fluid.

3. The cell analysis method according to claim 2, wherein the blood or biological fluid is brought into contact with a component having fibrinogen adsorbed thereto before being injected into the medical analysis device.

4. The cell analysis method according to claim 3,
wherein the component having fibrinogen adsorbed thereto is a blood collection syringe, a blood collection tube, or a centrifuge tube.

5. The cell analysis method according to claim 2, wherein the blood or biological fluid is centrifuged to remove at least one of a supernatant or a sediment before being injected into the medical analysis device.

* * * * *